United States Patent [19]

Ashman

[11] Patent Number: 5,403,315
[45] Date of Patent: Apr. 4, 1995

[54] POSITIONABLE SPINAL FIXATION DEVICE

[75] Inventor: Richard B. Ashman, Dallas, Tex.

[73] Assignee: Danek Medical, Inc., Memphis, Tenn.

[21] Appl. No.: 61,352

[22] Filed: May 13, 1993

Related U.S. Application Data

[63] Continuation of Ser. No. 875,734, Apr. 29, 1992, abandoned.

[51] Int. Cl.6 .......................... A61B 17/56; A61F 2/44
[52] U.S. Cl. .......................................... 606/61; 623/17
[58] Field of Search ...................... 606/60, 61, 72, 73, 606/74, 75, 76, 77; 623/16, 17

[56] References Cited

U.S. PATENT DOCUMENTS

| | | | |
|---|---|---|---|
| 3,565,066 | 2/1971 | Roaf | 606/61 |
| 3,596,656 | 8/1971 | Kaute | 606/71 |
| 4,338,926 | 7/1982 | Kummer | 606/70 |
| 4,433,677 | 2/1984 | Ulrich | 606/61 |
| 4,569,338 | 2/1986 | Edwards | 606/61 |
| 4,653,481 | 3/1987 | Howland | 606/61 |
| 4,957,495 | 9/1990 | Kluger | 606/61 |
| 4,987,892 | 1/1991 | Krug | 606/61 |
| 5,000,165 | 3/1991 | Watanabe | 606/61 |
| 5,067,955 | 11/1991 | Cotrel | 606/61 |
| 5,084,049 | 1/1992 | Asher | 606/73 |
| 5,152,303 | 10/1992 | Allen | 606/61 |
| 5,201,738 | 4/1993 | Scott | 606/77 |

*Primary Examiner*—Michael A. Brown
*Attorney, Agent, or Firm*—Woodard, Emhardt, Naughton, Moriarty & McNett

[57] ABSTRACT

A device is provided on spinal fixation hook or screw elements along a spinal implant rod for preventing or inhibiting them from unintentional sliding on the rod during handling prior to implantation in vivo. One embodiment uses a set screw in an eyebolt and which engages the rod. Another uses a plastic plug in an eyebolt and which engages the rod. A third uses a grooved aperture in the eyebolt cooperating with a grooved rod to inhibit unintentional sliding of the eyebolt on the rod.

13 Claims, 4 Drawing Sheets

POSITIONABLE SPINAL FIXATION DEVICE

This application is a continuation of application Ser. No. 07/875,734, filed Apr. 29, 1992, now abandoned.

BACKGROUND OF THE INVENTION

1. Field of the Invention

This invention relates to orthopedics and particularly to control of clamps and other accessories on spinal rods during implantation procedures.

2. Description of the Prior Art

During preparation for implantation of spinal fixation devices, various hooks and clamps are installed on a spinal rod. They are not fixed to the rod, since it is necessary to precisely locate and fix them only after placement in the body. But a spinal rod with an array of fixation devices loosely mounted thereon in preparation for implantation in the human body can be difficult to handle without the devices becoming significantly displaced and disoriented, even to the extent of sliding and falling off the end of the rod. For example, in the TSRH Spinal Implant System marketed by Danek Medical, Inc., the assignee of this application, a series of eyebolts which connect hooks, screws, and plates are positioned along a spinal rod. The connecting elements are used to attach these various hooks and screws to the rod at an infinite number of possible positions. As the surgeon approaches the patient with this plurality of fixation elements strung along the rod, there exists the opportunity for these eyebolt connecting elements to slide off one end of the rod. The ability to temporarily or provisionally position these eyebolts on the rod so that they do not lose their position, would significantly improve the system.

Prior art systems incorporating set screws on their fixation means already exist. Most of which I am aware use the set screws to fix the devices on the rod after they are suitably positioned in the body. They do not lend themselves to simply snugging the device on the rod during handling prior to implantation. Only one spinal fixation system of which I am aware possesses a fixation element which incorporates a means by which it can be temporarily held in position along a spinal fixation rod prior to implantation. It is the Cotrel Dubousset (C/D) instrumentation which uses a blocker which is essentially a cylindrical element with a set screw in it. This cylindrical element is used as the primary means of fixing hooks or screws to the spinal fixation rod. The set screw in the blocker is not only used to provisionally position the cylindrical element but also to provide final tightening of the blocker on the rod. An example is shown in Cotrel U.S. Pat. No. 4,641,636.

The C/D blocker significantly differs from the present invention in that, with the C/D blocker, the same set screw which is used to provisionally tighten the blocker is also used to provide final fixation on the rod. In contrast, various embodiments of the present invention include an eyebolt which uses a ¼" threaded fastener to provide final fixation. In accord with the present invention, the provisional tightening means does not alter this primary means of fixation between the eyebolt, rod and hooks or screws.

It is an object of the present invention to provide independent means to provisionally position a spinal fixation element on a long spinal fixation rod in order to facilitate final assembly of the implant system in vivo.

SUMMARY OF THE INVENTION

The present invention is illustrated in three embodiments herein. All three address the broad objective of this invention which is to simplify spinal surgery. More specifically, this is achieved through modification of existing fixation means to incorporate some means of provisionally tightening along the spinal implant rod but without compromising the strength of the fixation element.

One embodiment positions a set screw in the TSRH eyebolt fixation means so that the set screw engages the rod as the rod is sliding through the eyebolt, but without relying on the set screw for the final fixation. This involves some mechanical engagement between the eyebolt and the rod that can either be tightened or loosened, and requires a prevailing torsional or axial load other than mere weight of the parts, to initiate relative motion of the eyebolt on the rod.

Another embodiment incorporates a deformable member such as a plastic plug within the eyebolt and which engages the rod, thus requiring a specific prevailing axial or torsional load in order to initiate relative motion between the spinal rod and the fixation eyebolt.

The third embodiment uses a ribbed or threaded aperture in the eyebolt cooperating with a grooved rod to inhibit unintentional sliding of the eyebolt on the rod.

The three embodiments are intended to help the surgeon to be able to provisionally position and secure the eyebolts along the spinal rod, approximating the location of the specific hooks and screws that are to be implanted into the patients. In doing so, the final assembly of the device in vivo is made easier.

DESCRIPTION OF THE PREFERRED EMBODIMENT

Figure 1:
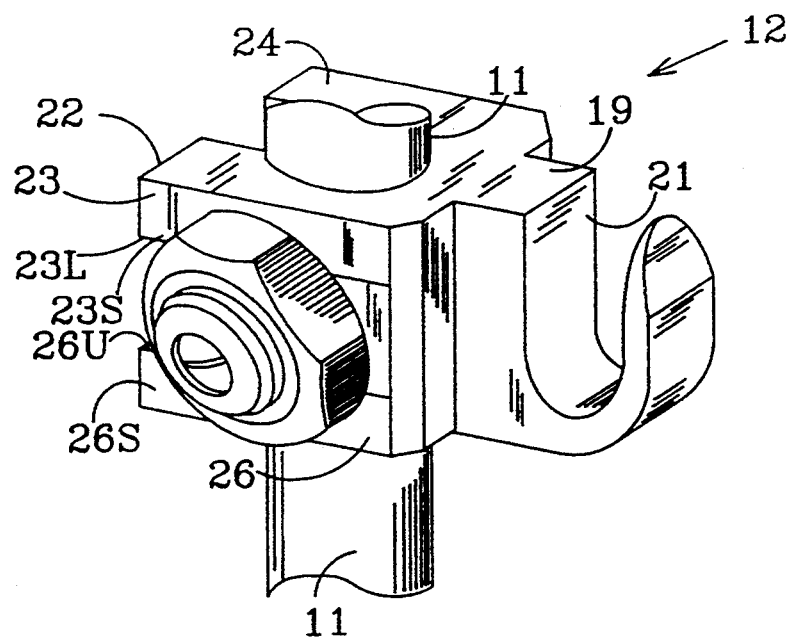
FIG. 1 is pictorial view of a combination eyebolt and hook with a spinal rod shown fragmentarily.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, FIG. 1 shows, fragmentarily, a spinal rod 11 with a fixation device 12 thereon of the so-called "three-point shear clamp mechanism" type employed in the TSRH Spinal System marketed by Danek Medical, Inc., the assignee of the present application. This mechanism includes an eyebolt 13 slidably received on the rod. The eyebolt includes a threaded shank 14 extending from the front face 16 of the eyebolt and receiving a nut 17 thereon. According to one embodiment of the present invention, a set screw 18 is threadedly received inside the shank.

Figure 2:
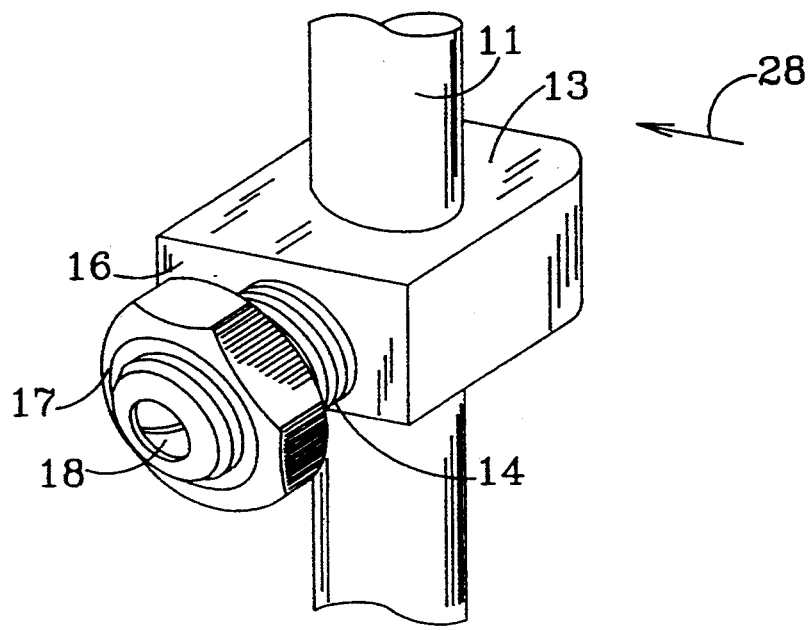
FIG. 2 is a pictorial view of time assembly of FIG. 1 but without the fixation hook.
Figure 3:
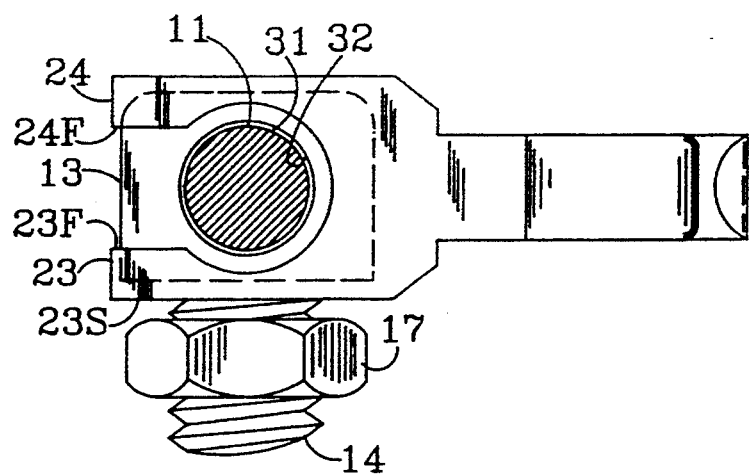
FIG. 3 is a cross section through the assembly of FIG. 1 taken immediately above the hook and showing the assembly loose on the spinal rod.
Figure 4:
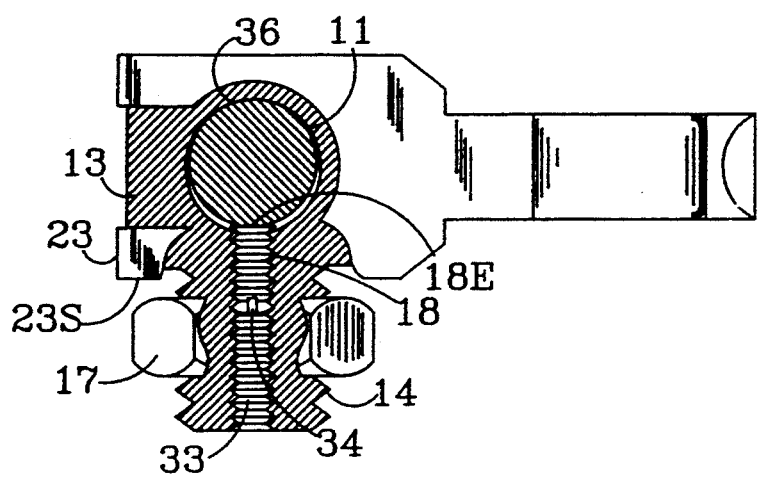
FIG. 4 is a cross sectional view similar to FIG. 3 but showing a portion of the upper arm of the hook broken away to show the interior construction of the eyebolt according to one embodiment of the present invention, with the eyebolt snug on the rod for provisional fixation but not yet clamping the hook to the rod.

According to the TSRH system, a hook or screw may be mounted to the eyebolt and clamped to it and to the spinal rod by tightening the nut 17 on the shank 14. In the illustrated embodiment here, the fixation device is a hook unit 19 including the hook portion 21 and a two-way yoke portion 22 having two upper arms 23 and 24 and two lower arms 26 and 27, the latter not being shown in the drawing but being directly below the upper arm 24 just as arm 26 is below arm 23. With the eyebolt 13 slidably mounted on the rod 11, the hook can be moved into position around the eyebolt by advancing it in the direction of arrow 28 (FIG. 2), the entrance spacing between the inside faces 23F and 24F of the upper arms and the corresponding spaces between the lower arms being just wide enough to admit the spinal rod into the yoke of the hook unit. Similarly, the vertical space between the lower face 23L of the upper arm 23 and the upper face 26U of the lower arm 26, and corresponding spaces between the other upper and lower arms are great enough to slidingly admit the eyebolt 13 into place as shown in FIGS. 1 and 3, for example. In this condition there is a slight clearance 31 between the center aperture 32 of the eyebolt, and the smooth outer cylindrical surface of the rod 11. This clearance is exaggerated in the drawing for purposes of illustration, but is just sufficient to permit the eyebolt to slide along the rod. At this time, the nut 17 is still out far enough on the eyebolt shank 14 that there was no interference of the nut with the installation of the hook unit on the eyebolt-rod combination. After the installation and proper positioning in the back of the patient, the nut 17 can be advanced on the shank until it clamps the fixation unit and eyebolt against the spinal rod. But it is during handling of the assembly prior to the installation, to which the present invention is addressed.

Figure 5:
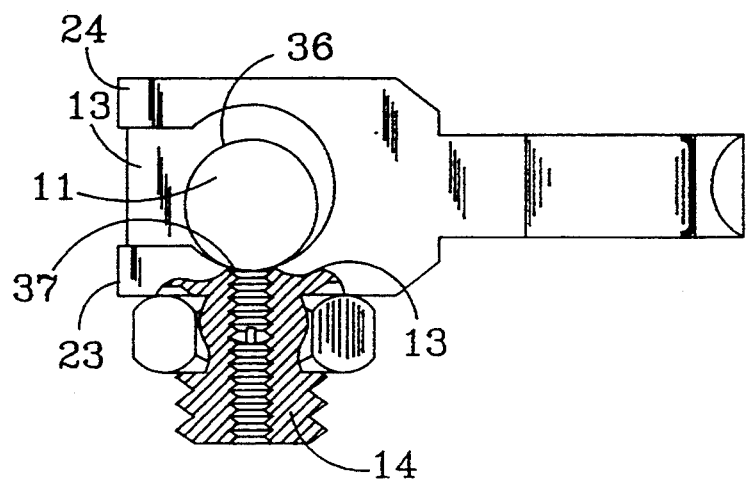
FIG. 5 is a view similar to FIG. 4 but showing the fixation hook and eyebolt clamped to each other and to the rod as in final fixation.

According to the first embodiment of the present invention, and in order to prevent the eyebolt from sliding along the rod during the handling of the rod prior to and during installation in vivo, the set screw 18 is threadedly received in the threaded hole 33 in the shank 14. The screw has a tool receiving recess 34 which, in the illustrated embodiment, is simply a screw driver slot to facilitate turning the set screw in so that its end 18E engages the rod 11 snugly enough to pull the eyebolt against the rod at the region 36 diametrically opposite the set screw. The tightness can be adjusted so that the eyebolt can be manually pushed along the rod by the surgeon if, and as desired, but will not slide along the rod due to its own weight or the weight of the hook unit when mounted to it. Then, after installation of the spinal rod assembly in the patient's body, the set screw can be loosened if and as desired to enable positioning the fixation hook exactly where desired after which it can be clamped in place on the spinal rod by advancing the nut 17 on the shank 14 until it clamps against the outer faces 23S and 26S of the upper and lower arms 23 and 26, respectively, of the hook unit. As it does so, it pulls the eyebolt toward the nut and tightly clamps the eyebolt region 36 against the rod diametrically opposite the shank and diametrically opposite the inner cylindrical surfaces of the upper and lower arms 23 and 26 such as at 37 in FIG. 5. In this way, the fixation element is securely clamped in place in the same manner as in the prior art fixation elements marketed by Danek Medical, Inc. But the management of the assembly prior to final clamping is made much easier. This can be particularly well appreciated when it is realized that five or six such fixation units may be mounted to a spinal rod before placement in the body and, the present invention, inhibiting the free sliding of each eyebolt along the rod makes it much easier to keep them in position on the rod during handling and placement in the body.

Figure 6:
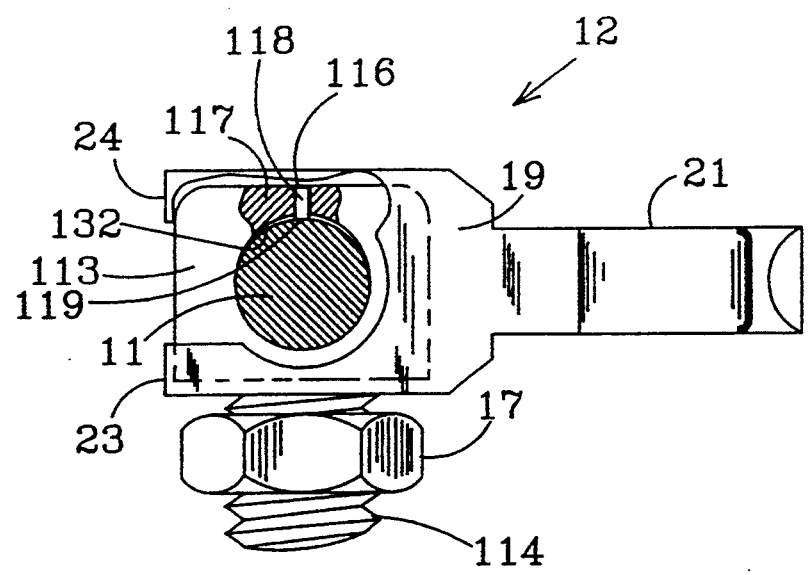
FIG. 6 is a view similar to FIG. 4 but showing a different embodiment using a plastic plug in the eyebolt to snug it on the rod.

Referring now to FIG. 6, components that are the same as in the previously described embodiment are given the same reference numerals. In this embodiment, however, the eyebolt 113 has an aperture 116 in the back wall 117 and in which a plastic polymer plug 118 is snugly received. The inner end 119 of this plug projects into the central aperture 132 of the eyebolt so that, as it is slipped onto the spinal rod 11, it is slightly deformed but snugly engages the rod 11 so that it cannot be moved or turned on the rod except by intentional externally applied force. The amount of initial extension or projection of the plastic plug into the aperture 132 can be determined in accord with the preferences of the attending surgeon, by selection of the particular material to be used and the tightness of the fit between the plug and the hole. It is intended that the plug not move in the hole 116 during the installation of the eyebolt on the spinal rod and that the frictional resistance of sliding of the eyebolt on the rod either in rotation or axially be controlled by the deformation of the plastic material itself. A nylon material would be suitable for the plug. The intent of the deformable polymer is to allow the eyebolt to be positioned along the rod such that it stays where it is left. In other words, the eyebolt will not alter its position unless a prevailing axial or torsional load has been applied to it. Final locking of the fixation between the hook or screw and the rod would then be accomplished in the standard fashion.

In the embodiment of FIG. 6, after the spinal rod with the assortment of eyebolts thereon has been placed in the body, the final positioning and clamping of the fixation element 12 is secured in the manner previously described by tightening the nut 17 against the faces of the upper and lower arms as described above with reference to FIG. 5. In this embodiment, of course, it is not necessary to have the threaded hole or set screw in the shank 114.

Figure 7:
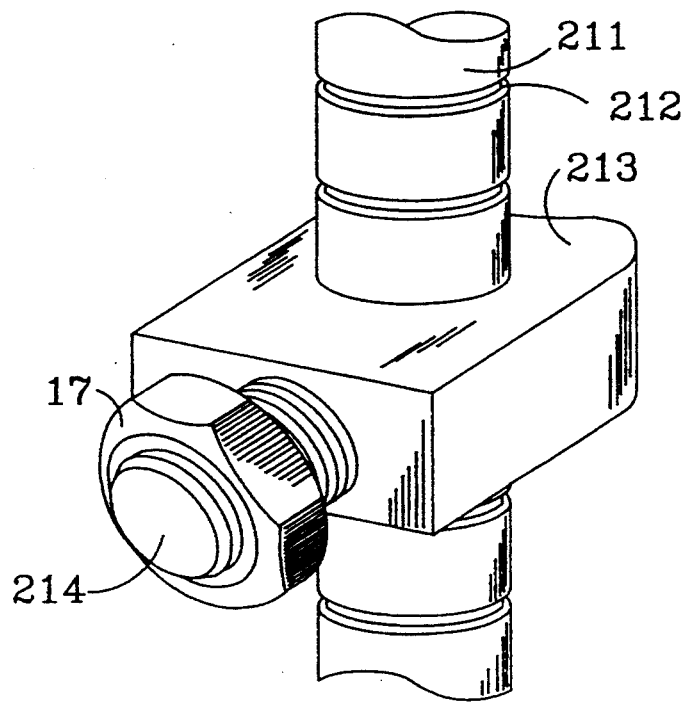
FIG. 7 is a pictorial view of a third embodiment of the eyebolt and spinal rod.
Figure 8:
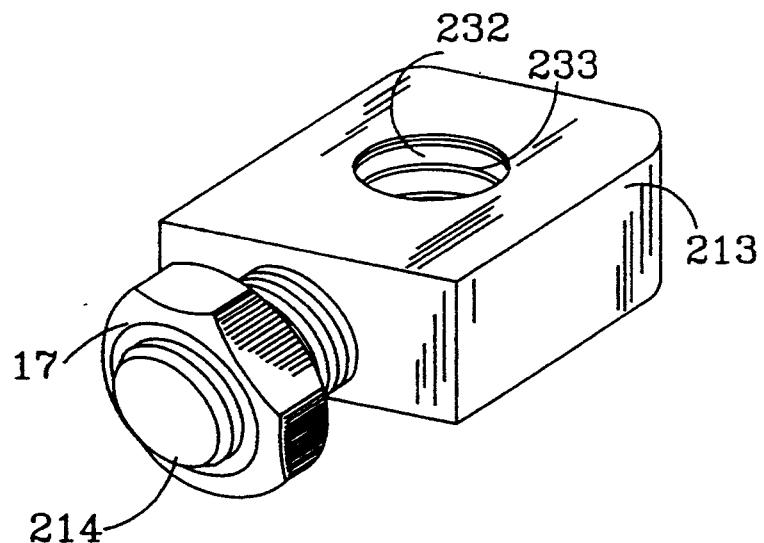
FIG. 8 is a pictorial view of the eyebolt itself.
Figure 9:
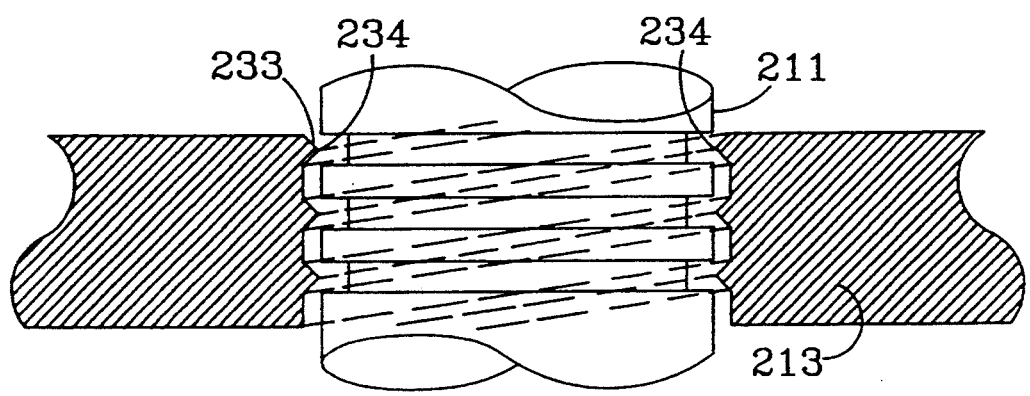
FIG. 9 is a section through a portion of the eyebolt at its interface with the spinal rod.

Referring now to FIGS. 7, 8 and 9, a further embodiment of the invention is shown. In this example, the spinal rod 211 is provided with axially spaced circumferential grooves 212 which may be of rectangular cross section. The eyebolt 213 is mounted on the rod and has a threaded shank 214 receiving the nut 17. But in this embodiment, the central aperture 232 of the eyebolt is different in the respect that it is provided with a spiral rib 233. The pitch of the spiral is such that the turns of rib are equally spaced at the same spacing as the grooves 212 in the spinal rod. Therefore the rib could be received in the grooves on at least one side of the rod as shown in FIG. 9 to inhibit the unintentional sliding and dislocation of the eyebolt on the rod. The internal diameter of the crests 234 of the ribs is slightly greater than the maximum outside diameter of the rod so that the eyebolts can be moved intentionally along the rod to the extent desired. The grooves are 0.005 to 0.010 inches deep on the rod itself. As in the prior two embodiments of the invention, final clamping of the assembly on the rod is done by tightening the nut 17 against the upper and lower arms 20 such as 23 and 26 of the fixation unit 12.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for engaging a fixation element along a spinal implant rod to permit provisionally tightening the fixation element on the rod prior to placement in vivo comprising:
    an eyebolt defining a central aperture adapted to receive a spinal rod therethrough;
    inhibitor means intersecting said central aperture of said eyebolt for provisionally positioning said eyebolt in a position on the rod and for inhibiting gravity induced free sliding of said eyebolt on the rod while permitting relative sliding between said eyebolt and the rod upon application of a determinate external force; and
    clamping means on the eyebolt, independent of the inhibitor means, for tightly clamping said eyebolt on the rod to prevent relative movement between said eyebolt and the rod by application of said determinate external force, and wherein;
    said eyebolt includes an externally threaded shank and said inhibitor means includes a set screw extending through said eyebolt shank and intersecting said central aperture to engage a rod extending therethrough sufficiently snugly to prevent said eyebolt from freely sliding relative to the rod, but without relying on said set screw for clamping said eyebolt on said rod.

2. The system of claim 1 and wherein:
    said clamping means include a nut threadedly received on said shank and operable thereon to clamp against a spinal fixation element mounted on eyebolt.

3. A system for engaging a fixation element along a spinal implant rod to permit provisionally tightening the fixation element on the rod prior to placement in vivo comprising:
    an eyebolt defining a central aperture adapted to receive a spinal rod therethrough;
    inhibitor means intersecting said central aperture of said eyebolt for provisionally positioning said eyebolt in a position on the rod and for inhibiting gravity induced relative free sliding between said eyebolt and the rod while permitting relative sliding between said eyebolt and the rod upon application of a determinate external force; and
    clamping means on the eyebolt, independent of the inhibitor means, for tightly clamping said eyebolt on the rod to prevent relative movement between said eyebolt and the rod by application of said determinate external force, and wherein;
    said inhibitor means includes a deformable polymeric plug mounted in said eyebolt and extending into said central aperture of said eyebolt sufficiently to interfere with the free sliding of said eyebolt relative to the rod.

4. The system of claim 3 and wherein:
    said eyebolt includes an externally threaded shank extending radially outward therefrom; and
    said deformable plug extends into said central aperture at a point thereon substantially diametrically opposite the location of said shank, said plug being resiliently deformed by the rod to frictionally resist movement of said eyebolt relative to the rod.

5. The system of claim 4 and wherein:
    said clamping means include a not threadedly received on said shank and operable thereon to clamp against a spinal fixation element mounted on said eyebolt.

6. A system for engaging a fixation element along a spinal implant rod to permit provisionally tightening the fixation element on the rod prior to placement in vivo comprising:
    an eyebolt defining a central aperture adapted to receive a spinal rod therethrough;
    inhibitor means intersecting said central aperture of said eyebolt for provisionally positioning said eyebolt in a position on the rod and for inhibiting gravity induced relative free sliding between said eyebolt and the rod while permitting relative sliding between said eyebolt and the rod upon application of a determinate external force; and
    clamping means on the eyebolt, independent of the inhibitor means, for tightly clamping said eyebolt on the rod to prevent relative movement between said eyebolt and the rod by application of said determinate external force, and wherein;
    said inhibitor means include an inwardly projecting rib defined in said central aperture of said eyebolt.

7. The system of claim 6 and wherein:
    said inhibitor means include longitudinally spaced circumferential grooves in the exterior of the rod for engagement by said rib of said eyebolt to inhibit free sliding of said eyebolt along the rod.

8. The system of claim 7 and wherein:
    said rib is a spiral rib, and the pitch of said rib spiral is equal to the spacing between said grooves.

9. The system of claim 8 and wherein:
    said clamping means include a nut threadedly received on said shank and operable thereon to clamp against a spinal fixation element mounted on said eyebolt.

10. A spinal rod system for implantation in the spine of the patient comprising:
    a spinal rod configured to extend adjacent the spine;
    means for engaging said rod to a vertebra of the spine, said means including;
    a component having an aperture receiving said rod therethrough;
    clamping means carried by said component for clamping said component to said rod by a clamping force acting on said rod; and
    inhibitor means, carried by said component and acting separate from said clamping means against said rod at said aperture, for provisionally positioning said component on said rod by inhibiting gravity induced relative free sliding between said component and said rod while permitting relative movement between said component and said rod upon application of a determinate external force less than said clamping force.

11. The spinal rod system of claim 10, wherein:
said means for engaging said rod to a vertebra includes a fixation element having a vertebra engaging portion and a rod engaging portion; and said component is an eyebolt having a body defining said aperture and including an externally threaded shank extending from said body for receiving a threaded nut thereon,
said rod engaging portion of said fixation element receiving said externally threaded shank therethrough whereby said component and said fixation element are clamped to said rod by tightening said nut onto said threaded shank.

12. The spinal rod system of claim 10, wherein said inhibitor means includes a set screw extending through said eyebolt shank and intersecting said aperture to act against said rod when said set screw is threaded into said eyebolt shank.

13. The spinal rod system of claim 10 wherein said inhibitor means includes an inwardly projecting rib in said aperture for frictionally engaging said rod extending therethrough.

* * * * *

UNITED STATES PATENT AND TRADEMARK OFFICE
CERTIFICATE OF CORRECTION

PATENT NO. : 5,403,315
DATED : April 4, 1995
INVENTOR(S) : Richard B. Ashman

It is certified that error appears in the above-identified patent and that said Letters Patent is hereby corrected as shown below:

Column 6, line 17, please change "not" to "nut".

Signed and Sealed this

Fifth Day of December, 1995

Attest:

BRUCE LEHMAN

Attesting Officer   Commissioner of Patents and Trademarks